(12) United States Patent
Mandaogade et al.

(10) Patent No.: US 8,962,016 B2
(45) Date of Patent: *Feb. 24, 2015

(54) EXTENDED RELEASE DOSAGE FORMS OF METOPROLOL

(75) Inventors: Prashant Manohar Mandaogade, Amravati (IN); Venkatesh Madhavacharya Joshi, Raichur (IN); Saurabh Srivastava, Allahabad (IN); Vinayak Dinkar Kadam, Ahmednagar (IN); Girish Kumar Jain, Delhi (IN)

(73) Assignee: Wockhardt Ltd., Bandra East, Mumbai (IN)

( * ) Notice: Subject to any disclaimer, the term of this patent is extended or adjusted under 35 U.S.C. 154(b) by 0 days.

This patent is subject to a terminal disclaimer.

(21) Appl. No.: 12/954,644

(22) Filed: Nov. 25, 2010

(65) Prior Publication Data

US 2011/0070300 A1    Mar. 24, 2011

Related U.S. Application Data

(63) Continuation of application No. 12/225,746, filed as application No. PCT/IB2007/000776 on Mar. 28, 2007, now Pat. No. 8,815,285.

(30) Foreign Application Priority Data

Mar. 28, 2006 (IN) .......................... 452/MUM/2006
Mar. 28, 2006 (IN) .......................... 453/MUM/2006
Sep. 29, 2006 (IN) ........................ 1600/MUM/2006

(51) Int. Cl.
*A61K 9/48*    (2006.01)
*A61K 9/00*    (2006.01)
*A61K 9/20*    (2006.01)
*A61K 9/50*    (2006.01)
*A61K 31/435*  (2006.01)
*A61K 31/138*  (2006.01)
*A61K 31/554*  (2006.01)
*A61K 31/18*   (2006.01)

(52) U.S. Cl.
CPC ............ *A61K 31/138* (2013.01); *A61K 9/2077* (2013.01); *A61K 9/5047* (2013.01); *A61K 9/5078* (2013.01); *A61K 9/2031* (2013.01); *A61K 9/2054* (2013.01)
USPC ........... 424/452; 424/400; 424/465; 424/495; 514/338; 514/652; 514/651; 514/211.07; 514/603

(58) Field of Classification Search
CPC .. A61K 9/2031; A61K 9/2054; A61K 9/5047
See application file for complete search history.

(56) References Cited

U.S. PATENT DOCUMENTS

| | | | | |
|---|---|---|---|---|
| 5,188,841 A | * | 2/1993 | Simpkin et al. | 424/495 |
| 5,384,130 A | * | 1/1995 | Kamada | 424/461 |
| 6,149,943 A | * | 11/2000 | McTeigue et al. | 424/494 |
| 6,808,721 B2 | * | 10/2004 | Cappola et al. | 424/474 |
| 2003/0228361 A1 | * | 12/2003 | Baichwal et al. | 424/468 |
| 2004/0198838 A1 | * | 10/2004 | Alles et al. | 514/651 |
| 2005/0008701 A1 | * | 1/2005 | Sriwongjanva et al. | 424/469 |
| 2005/0266079 A1 | * | 12/2005 | Achanta et al. | 424/471 |

OTHER PUBLICATIONS

Maganti et al. in International Journal of Pharmaceutics 103, 55-67 (1994).*

* cited by examiner

*Primary Examiner* — Dennis Heyer
(74) *Attorney, Agent, or Firm* — Bio Intellectual Property Services LLC (Bio IPS); O. (Sam) Zaghmout

(57) ABSTRACT

The present invention relates to extended release dosage forms of metoprolol or salts thereof comprising a water insoluble and non-swellable inert core and one or more pharmaceutically acceptable excipients. The invention also relates to processes for the preparation of an inert core and extended release dosage forms.

17 Claims, No Drawings

EXTENDED RELEASE DOSAGE FORMS OF METOPROLOL

CROSS-REFERENCE TO RELATED APPLICATIONS

This application is a continuation of U.S. application Ser. No. 12/225,746, filed Apr. 13, 2009, now U.S. Pat. No. 8,815,285, which entered the National Phase of Serial No. PCT/IB2007/000776, filed Mar. 28, 2007, which claims benefit of an Indian Patent Application No. 1600/MUM/2006, filed Sep. 29, 2006; an Indian Patent Application No. 453/MUM/2006, filed Mar. 28, 2006; and an Indian Patent Application No. 452/MUM/2006, filed Mar. 28, 2006. The entire disclosure of these prior applications are hereby incorporated by reference.

FEDERALLY SPONSORED RESEARCH

Not Applicable.

SEQUENCE LISTING OR PROGRAM

Not Applicable.

FIELD OF THE INVENTION

The present invention relates to extended release dosage forms of metoprolol or salts thereof comprising a water insoluble and non-swellable inert core and one or more pharmaceutically acceptable excipients. The invention also relates to processes for the preparation of an inert core and extended release dosage forms.

BACKGROUND OF THE INVENTION

Metoprolol is a beta1-selective (cardioselective) adrenoceptor blocking agent. It is commercially available in two salt forms; one of them is tartrate salt available as Lopressor tablets and the other is succinate salt (Formula I) available as Toprol-XL tablets. Metoprolol is chemically, (±) 1-(isopropylamino)-3-[p-(2-methoxyethyl) phenoxy]-2-propanol. Metoprolol succinate is indicated in the treatment of hypertension, angina pectoris and heart failure.

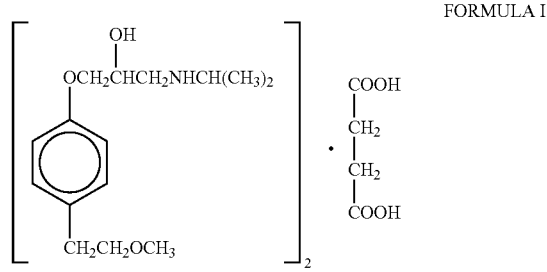

FORMULA I

U.S. Pat. Nos. 4,927,640 and 4,957,745 disclose a controlled release preparation containing a number of beads comprising insoluble cores coated with metoprolol. The beads have a high content of metoprolol in the range of 95-100% w/w of the soluble part of the bead. Insoluble cores, such as glass and silicon dioxide are used.

U.S. Pat. No. 5,001,161 discloses a pharmaceutical composition comprising metoprolol succinate together with a sustained release pharmaceutically acceptable carrier.

U.S. Patent Publication 20030185887 discloses a controlled or sustained release dosage formulation of propranolol where the inert core is coated with a solution of propranolol, water insoluble binder and filler. The active core so produced is further coated with a release-controlling layer.

U.S. Patent Publication 20050008701 discloses a controlled release pellet comprising water-soluble or water swellable inert core and a drug layer applied to it, along with a controlled release coating surrounding the drug layer International (PCT) Publication WO2005084636 discloses an oral controlled-release pharmaceutical composition of metoprolol succinate comprising a water-soluble, water swellable or water-insoluble inert core; one or more drug layers comprising metoprolol and one or more polymeric coatings surrounding the one or more drug layers. The water-soluble inert core comprises sugar sphere or salt, water insoluble inert core comprises silicon dioxide, small particles of glass, plastic resin particles or mixtures thereof and water swellable inert core comprises hydroxypropyl methylcellulose, microcrystalline cellulose, starch or mixture thereof.

Several other controlled release/extended release pharmaceutical compositions are known for example, in U.S. Pat. Nos. 5,399,362; 5,399,358; 5,707,656; 5,709,882; and 4,871,549; U.S. Application Nos. 20020177579; 20050266078; 20060003007; and 20040228915.

SUMMARY OF THE INVENTION

In one general aspect there is provided an inert core for preparation of a solid oral dosage form wherein, the core comprises microcrystalline cellulose spheres coated with one or more water insoluble pharmaceutically acceptable polymers, the inert core further comprise one or more coatings with one or more pharmaceutically active ingredients and other pharmaceutically acceptable excipients, which is optionally coated with one or more release controlling polymers.

The phrase "inert core," as used herein, includes core that is water insoluble and non-swellable.

The phrase "solid oral dosage form," as used herein, refers to tablets, capsules, pellets, sachets, and the like.

The phrase "insoluble," as used herein, refers to inert core, which does not dissolve in water.

The pharmaceutically active ingredients comprise one or more of lansoprazole, pantoprazole, metoprolol, propranolol, diltiazem, tamsulosin, diclofenac, itraconazole, venlafaxine, tolterodine and pharmaceutically acceptable salts or derivatives thereof.

The pharmaceutically acceptable polymer comprises one or more of acrylic polymers or copolymers, ethylcellulose and like.

The release controlling polymers comprises one or more of cellulose ethers and acrylic acid polymers.

Embodiments of the dosage form comprises one or more of the following features. For example, the dosage form comprises other pharmaceutically acceptable excipients. The other excipients comprise one or more of fillers, binders, superdisintegrants, disintegrants, lubricants, glidants, plasticizers, anti-adherents, aqueous or non-aqueous solvents, cushioning agents, polymers and the like.

In another general aspect there is provided an extended release dosage form of metoprolol or salts thereof comprising an inert core comprising microcrystalline cellulose spheres coated with a polymer optionally having other pharmaceutically acceptable excipients, the inert core is further coated with drug comprising metoprolol or salt thereof optionally having other pharmaceutically acceptable excipients, the drug coat is further coated with one or more pharmaceutically acceptable rate-controlling polymer to give a desired release profile.

The pharmaceutically acceptable rate-controlling polymer comprises one or more of cellulose ethers and acrylic acid polymers.

Embodiments of the dosage form comprise one or more of the following features. For example, the dosage form comprises other pharmaceutically acceptable excipients. The other excipients comprises one or more of fillers, binders, superdisintegrants, disintegrants, lubricants, glidants, plasticizers, anti-adherents, aqueous or non-aqueous solvents, cushioning agents, polymers and the like.

In another general aspect there is provided a dosage form comprising an inert core comprising one or more pharmaceutically active ingredients and one or more pharmaceutically acceptable excipients or an inert core coated with one or more pharmaceutically active ingredients and one or more pharmaceutically acceptable excipients, which is optionally further coated with one or more pharmaceutically acceptable release controlling polymers and then coated with colloidal silicon dioxide.

Colloidal silicon dioxide minimizes crushing of pellets during tablet compression. Thus present invention provides a method for minimizing crushing of pellets.

The pharmaceutically active ingredients comprise one or more of lansoprazole, pantoprazole, metoprolol, propranolol, diltiazem, tamsulosin, diclofenac, itraconazole, venlafaxine, tolterodine and pharmaceutically acceptable salts or derivatives thereof.

The pharmaceutically acceptable release controlling polymers comprises one or more of cellulose ethers and acrylic acid polymers.

Embodiments of the dosage form comprises one or more of the following features. For example, the dosage form comprises one or more pharmaceutically acceptable excipients. The excipients comprises one or more of fillers, binders, superdisintegrants, disintegrants, lubricants, glidants, plasticizers, anti-adherents, aqueous or non-aqueous solvents, cushioning agents, polymers and the like.

In another general aspect there is provided an extended release dosage form of metoprolol or salt thereof comprising an inert core comprising metoprolol or salt thereof and one or more pharmaceutically acceptable excipients or an inert core coated with metoprolol or salt thereof and one or more pharmaceutically acceptable excipients, which is optionally further coated with one or more pharmaceutically acceptable release controlling polymers to impart desired release profile and then coated with colloidal silicon dioxide.

Colloidal silicon dioxide minimizes crushing of pellets during tablet compression. Thus present invention provides a method for minimizing crushing of pellets.

The pharmaceutically acceptable release controlling polymers comprises one or more of cellulose ethers and acrylic acid polymers.

Embodiments of the dosage form comprises one or more of the following features. For example, the dosage form comprises one or more pharmaceutically acceptable excipients. The excipients comprises one or more of fillers, binders, superdisintegrants, disintegrants, lubricants, glidants, plasticizers, anti-adherents, aqueous or non-aqueous solvents, cushioning agents, polymers and the like.

In another general aspect there is provided an inert core for preparation of solid oral dosage form, wherein the inert core is insoluble and non-swellable and comprises microcrystalline cellulose spheres coated with one or more pharmaceutically acceptable polymers in admixture with one or more pharmaceutically acceptable excipients.

The present invention provides a water insoluble and non-swellable inert core.

The phrase "insoluble," as used herein, refers to inert core, which does not dissolve in water.

The phrase "non-swellable," as used herein, refers to inert core having 20% or less swelling after 24 hours.

The pharmaceutically acceptable polymer comprises one or more of acrylic polymers or copolymers, ethylcellulose and like.

Embodiments of the dosage form comprises one or more of the following features. For example, the dosage form comprises one or more pharmaceutically acceptable excipients. The excipients comprises one or more of fillers, binders, superdisintegrants, disintegrants, lubricants, glidants, plasticizers, anti-adherents, aqueous or non-aqueous solvents, cushioning agents, polymers and the like.

In another general aspect there is provided an extended release dosage form of metoprolol or salt thereof comprising plurality of beads comprising
  a) water insoluble and water non-swellable inert core;
  b) one or more drug layers comprising metoprolol or salt thereof in admixture with pharmaceutically acceptable excipients;
  c) one or more pharmaceutically acceptable rate controlling polymer surrounding one or more drug layers; and
  d) optionally one or more non functional coatings surrounding the one or more polymeric coatings The phrase "insoluble," as used herein, refers to inert core, which does not dissolve in water.

The phrase "non-swellable," as used herein, refers to inert core having 20% or less swelling after 24 hours.

The pharmaceutically acceptable rate controlling polymers comprises one or more of cellulose ethers and acrylic acid polymers.

Embodiments of the dosage form comprises one or more of the following features. For example, the dosage form comprises one or more pharmaceutically acceptable excipients. The excipients comprises one or more of fillers, binders, superdisintegrants, disintegrants, lubricants, glidants, plasticizers, anti-adherents, aqueous or non-aqueous solvents, cushioning agents, polymers and the like.

The non functional coatings comprise one or more of polyethylene glycols and colloidal silicon dioxide.

In another general aspect there is provided an extended release dosage form of metoprolol or salt thereof comprising plurality of beads wherein the dosage form comprise water insoluble and water non-swellable inert core, the inert core is further coated with metoprolol or salt thereof which is further coated with one or more pharmaceutically acceptable rate-controlling polymer.

The phrase "insoluble," as used herein, refers to inert core, which does not dissolve in water.

The phrase "non-swellable," as used herein, refers to inert core having 20% or less swelling after 24 hours.

The pharmaceutically acceptable rate controlling polymers comprises one or more of cellulose ethers and acrylic acid polymers.

Embodiments of the dosage form comprises one or more of the following features. For example, the dosage form comprises one or more pharmaceutically acceptable excipients. The excipients comprises one or more of fillers, binders, superdisintegrants, disintegrants, lubricants, glidants, plasticizers, anti-adherents, aqueous or non-aqueous solvents, cushioning agents, polymers and the like.

DETAILED DESCRIPTION OF THE INVENTION

The inventors have found that microcrystalline cellulose pellets (Celphere CP 203) that is water swellable, when coated with water insoluble polymer ethylcellulose (Ethocel) layer in admixture with one or more pharmaceutically acceptable excipients comprising plasticizer and solvent can be used as an inert core. The formed inert core was found to be water insoluble and non-swellable. The inert core further coated with one or more drug layers, further coated with one or more release controlling layers to provide controlled release, sustained release or extended release dosage forms. The inventors have also found that an extended release pellets of metoprolol or salt thereof when coated with colloidal silicon dioxide (Aerosil 200) crushing of pellets during tablet compression was minimized.

The inert core also called as seal coat can be used to prepare immediate release, extended release, controlled release or sustained release dosage forms of various categories of drugs. Microcrystalline cellulose spheres are water swellable however the present invention provides a non-swellable inert core that is prepared by coating microcrystalline cellulose spheres with ethylcellulose in admixture with plasticizer, anti-adherent and suitable solvent. Also the inert core of present invention is water insoluble. The inert core is prepared by dissolving Ethocel and triacetin in suitable solvent and then Celphere CP 203 is coated with it in fluid bed processor at optimum parameters.

The extended release dosage form comprises metoprolol as an active ingredient, which is present in the form of metoprolol succinate. The extended release dosage form of metoprolol succinate is prepared using a water insoluble and water non-swellable inert core wherein an inert core comprises of microcrystalline cellulose spheres coated with water insoluble polymer ethylcellulose in admixture with one or more of plasticizer, anti-adherent and solvent. The inert core is further coated with a drug solution or suspension comprising drug, opadry and suitable solvent, in fluid bed processor at optimum parameters. The drug layer is further coated in fluid bed processor at optimized parameters with an extended release coat wherein one or more pharmaceutically acceptable rate controlling polymers are dissolved in a suitable solvent. The coated pellets are further blended in suitable blender with one or more pharmaceutically acceptable excipients comprising one or more of fillers, superdisintegrants, lubricants, glidants and the like. The pellets are further compressed to form tablets using suitable tooling.

The extended release coated pellets are further coated with Aerosil coat. The Aerosil coat is prepared by mixing Opadry and colloidal silicon dioxide (Aerosil 200) in suitable solvent and then coating the extended release coated pellets with it in fluid bed processor at optimum parameters. The Aerosil coated pellets are further blended in suitable blender with one or more pharmaceutically acceptable excipients comprising one or more of fillers, superdisintegrants, lubricants, glidants and the like. The pellets are further compressed to form tablets using suitable tooling.

The extended release coated pellets is further coated with one or more non-functional coatings. The non-functional coating comprises one or more of Polyethylene glycol (PEG) and colloidal silicon dioxide. The PEG coated pellets are further blended in suitable blender with one or more pharmaceutically acceptable excipients comprising one or more of fillers, superdisintegrants, lubricants, glidants, cushioning agents and the like. The obtained blend can be optionally compressed to form tablet using suitable tooling or filled into capsule.

The pharmaceutically acceptable rate controlling polymers comprises one or more of cellulose ethers, acrylic acid polymers and mixtures, thereof. Suitable cellulose ethers comprises one or more of hydroxypropyl methylcellulose, hydroxypropyl cellulose and other suitable cellulose ethers. Suitable acrylic acid polymers comprises one or more of polyacrylic acid polymers or carboxyvinyl polymers such as those available under the brand name Carbopol.

The pharmaceutically acceptable excipients comprises one or more of fillers, binders, superdisintegrants, disintegrants, lubricants, glidants, plasticizers, anti-adherents, aqueous or non-aqueous solvents, cushioning agents, polymers and the like.

The fillers comprise one or more of Avicel PH 101, Avicel PH 102, lactose, and dicalcium phosphate.

The binder comprise one or more of hydroxypropyl methylcellulose, povidone, hydroxypropyl cellulose, ethylcellulose or mixtures thereof.

The Superdisintegrant comprise one or more of croscarmellose sodium, crospovidone and sodium starch glycolate.

The Disintegrant comprise one or more of croscarmellose sodium, crospovidone and sodium starch glycolate.

The Lubricants comprise one or more of magnesium stearate, calcium stearate, and sodium benzoate.

The glidants comprise be one or more of colloidal silicon dioxide and talc.

The plasticizers comprise one or more of diethyl phthalate, triethyl citrate, acetyl tributyl citrate, dibutyl phthalate, triacetin, propylene glycol, polyethylene glycol and the like.

The anti-adherent comprise one or more of talc.

The solvents comprise one or more of dichloromethane, acetone, ethanol, methanol, isopropyl alcohol, water or mixture thereof.

The Cushioning agent comprise one or more of PEG, colloidal silicon dioxide and the like.

The Non-functional coating comprises one or more of Polyethylene glycols (PEGs), colloidal silicon dioxide and the like.

The present invention is further illustrated by the following examples which are provided merely to be exemplary of the invention and do not limit the scope of the invention. Certain modifications and equivalents will be apparent to those skilled in the art and are intended to be included within the scope of the present invention.

Example 1

Table 1 provides composition of batches of the present invention.

TABLE 1

| S. No. | Ingredients | mg/tablet |
|---|---|---|
| Stage 1: Seal Coating | | |
| 1. | Celphere CP 203 | 43.50 |
| 2. | Ethocel | 2.18 |
| 3. | Triacetin | 0.22 |
| Stage 2: Drug Layering | | |
| 4. | Metoprolol Succinate | 190.00 |
| 5. | Opadry YS-1R-7006 Clear | 19.00 |

TABLE 1-continued

| S. No. | Ingredients | mg/tablet |
|---|---|---|
| | Stage 3: Extended Release Coating | |
| 6. | Ethocel | 27.32 |
| 7. | Opadry YS-1R-7006 Clear | 6.83 |
| | Stage 4 Blending and Compression | |
| 8. | Extended Release Coated Pellets | 289.05 |
| 9. | Avicel PH 101 | 332.49 |
| 10. | Avicel PH 102 | 110.82 |
| 11. | Polyethylene Glycol 6000 | 133.90 |
| 12. | Ac-di-sol | 79.60 |
| 13. | Aerosil 200 | 1.20 |
| 14. | Magnesium stearate | 2.94 |
| | Total | 950.00 |

Procedure: Ethocel and triacetin were dissolved in a suitable solvent and Celphere CP 203 was coated in fluid bed processor at optimum parameters with the above mixture. Metoprolol succinate and opadry clear were dissolved in suitable solvent and seal coated pellets were coated with it in fluid bed processor at optimum parameters. Ethocel and opadry clear were dissolved in a suitable solvent and drug layered pellets were coated with it in fluid bed processor at optimized parameters. Avicel PH 101, Avicel PH 102, Polyethylene glycol 6000, Ac-di-sol (croscarmellose sodium) and Aerosil 200 were sifted through suitable mesh and then blended in suitable blender. Magnesium stearate was sifted through suitable mesh. The blend was lubricated and Extended Release coated pellets were transferred to blender and blended. The Pellets were compressed to form tablets using suitable tooling.

Table 2 provides the dissolution data of the tablets prepared as per the Formula provided in Table 1. For determination of drug release rate, USP Type 2 Apparatus, 50 rpm was used wherein 500 ml of phosphate buffer pH 6.8 was used as a medium.

TABLE 2

| Time (hour) | % Drug released |
|---|---|
| 0 | 0 |
| 1 | 13 |
| 2 | 23 |
| 4 | 41 |
| 8 | 66 |
| 12 | 84 |
| 16 | 92 |
| 20 | 97 |

Example 2 and 3

Table 3 provides composition of batches of the present invention.

TABLE 3

| Stages | Ingredients | Example 2 mg/tablet | Example 3 mg/tablet |
|---|---|---|---|
| Stage 1: Seal Coating | Celphere CP 203 | 43.50 | 43.50 |
| | Ethocel | 2.18 | 2.18 |
| | Triacetin | 0.22 | 0.22 |
| Stage 2: Drug Layering | Metoprolol Succinate | 190.00 | 190.00 |
| | Opadry YS-1R-7006 Clear | 19.00 | 19.00 |
| Stage 3: Extended Release Coating | Ethocel | 27.32 | 27.32 |
| | Opadry YS-1R-7006 Clear | 6.83 | 6.83 |
| Stage 4: Colloidal silicon dioxide Coating (Aerosil) | Aerosil 200 | — | 19.25 |
| | Opadry YS-1R-7006 Clear | — | 2.14 |
| Stage 5: Blending and Compression | Extended Release Coated Pellets | 289.05 | — |
| | Aerosil Coated Pellets | — | 310.44 |
| | Avicel PH 101 | 332.49 | 321.55 |
| | Avicel PH 102 | 110.82 | 107.19 |
| | Polyethylene Glycol 6000 | 133.90 | 129.73 |
| | Ac-di-sol | 79.60 | 77.11 |
| | Aerosil 200 | 1.20 | 1.14 |
| | Magnesium stearate | 2.94 | 2.84 |
| | Total | 950.00 | 950.00 |

Procedure: Ethocel and triacetin were dissolved in suitable solvent and Celphere CP 203 was coated with it in fluid bed processor at optimum parameters. Metoprolol succinate and opadry were dissolved in suitable solvent and seal coated pellets were coated with it in fluid bed processor at optimum parameters. Ethocel and opadry were dissolved in suitable solvent and drug-layered pellets were coated with it in fluid bed processor at optimized parameters. Opadry and Aerosil 200 (colloidal silicon dioxide) were added to suitable solvent and then extended release pellets were coated with it in fluid bed processor at optimum parameters in case of example 3. Avicel PH 101, Avicel PH 102, Polyethylene glycol 6000, Ac-di-sol (croscarmellose sodium) and Aerosil 200 were sifted through suitable mesh and then blended in suitable blender. Magnesium stearate was sifted through suitable mesh. The blend was lubricated in suitable blender. The Aerosil-coated pellets were transferred to suitable blender and blended. Pellets were compressed to form tablets using suitable tooling.

Table 4 provides the dissolution data of the tablets prepared as per the Formula provided in Table 3. For determination of drug release rate, USP Type 2 Apparatus, 50 rpm was used wherein 500 ml of phosphate buffer pH 6.8 was used as a medium.

TABLE 4

| Time (hour) | Example 2 % Drug released | Example 3 % Drug released |
|---|---|---|
| 0 | 0 | 0 |
| 1 | 13 | 5 |
| 2 | 23 | 11 |
| 4 | 41 | 24 |
| 8 | 66 | 52 |
| 12 | 84 | 72 |
| 16 | 92 | 86 |
| 20 | 97 | 93 |

Example 4

Table 5 provides % swelling in coated and uncoated microcrystalline pellets (Celphere CP 203 and Celphere CP 305)

TABLE 5

| S. No. | Celphere Type | Initial volume (mL) | Volume after 24 hrs (mL) | % Swelling |
|---|---|---|---|---|
| 1. | Uncoated Celphere CP 203 | 4 | 6 | 50 |
| 2. | Coated* Celphere CP 203 | 4 | 4.7 | 17.5 |
| 3. | Uncoated Celphere CP 305 | 4 | 6.2 | 55 |
| 4. | Coated* Celphere CP 305 | 4 | 4.6 | 15 |

*Ethylcellulose coat that is 15% of the uncoated Celphere CP 203 & Celphere CP 305

Procedure: All coated and uncoated Celphere pellets were separately put in measuring cylinder occupying 4 ml volume. To each cylinder was added 4 ml water and was kept for 24 hr period at controlled room temperature. After 24 hrs increase in the volume was measured and % swelling was calculated. The coated Celphere CP 203 and CP 305 showed % swelling of 20% or less in 24 hrs.

Example 5

Table 6 provides composition of batches of the present invention.

TABLE 6

| S. No. | Ingredients | mg/tablet |
|---|---|---|
| Stage 1: Seal Coating | | |
| 1. | Celphere CP 305 | 43.5 |
| 2. | Ethylcellulose 50 cps | 4.94 |
| 3. | Triethyl citrate | 0.494 |
| 4. | Talc | 1.087 |
| Stage 2: Drug Layering | | |
| 5. | Metoprolol Succinate | 190 |
| 6. | Opadry Clear | 19 |
| Stage 3: Extended Release Coating | | |
| 7. | Ethylcellulose | 14.5 |
| 8. | Opadry Clear | 3.63 |
| Stage 4: PEG Coating | | |
| 9. | PEG Coating | 27.715 |
| Stage 5: Blending and Compression | | |
| 10. | PEG coated pellets | 304.8 |
| 11. | Prosolv SMCC 90 | 517.72 |
| 12. | Croscarmellose NA | 70 |
| 13. | PEG 6000 | 104.28 |
| 14. | Sodium stearyl fumarate | 3.2 |
| | Total Tablet Weight | 1000 |

Procedure: Ethylcellulose was dissolved in a suitable solvent and to it triethyl citrate and talc were added. Celphere CP 305 spheres were coated in fluid bed processor at optimum parameters with the above prepared mixture to get seal coated pellets. Metoprolol succinate and opadry clear were dissolved in suitable solvent and seal coated pellets were coated with it in fluid bed processor at optimum parameters. Ethylcellulose and opadry clear were dissolved in suitable solvent and drug layered pellets were coated with it in fluid bed processor at optimized parameters. The polymer coated pellets were then coated with PEG in suitable solvent followed by blending the PEG coated pellets with presifted Prosolv SMCC 90, croscarmellose sodium, PEG 6000 in suitable blender. The obtained blend was lubricated with presifted Sodium stearyl fumarate and compressed to form tablets using suitable tooling.

While the present invention has been described in terms of its specific embodiments, certain modifications and equivalents will be apparent to those skilled in the art and are intended to be included within the scope of the present invention.

We claim:

1. A water insoluble and water non-swellable inert core for preparation of a solid oral dosage form, wherein the core comprises microcrystalline cellulose spheres coated with one or more water insoluble pharmaceutically acceptable polymers with the proviso that said inert core does not include an active ingredient.

2. The inert core of claim 1, wherein the water insoluble pharmaceutically acceptable polymer is ethylcellulose.

3. The inert core of claim 1 further comprising one or more coatings with one or more pharmaceutically active ingredients and other pharmaceutically acceptable excipients, which is optionally further coated with one or more release controlling polymers.

4. The inert core of claim 3, wherein the pharmaceutically active ingredient comprises metoprolol and pharmaceutically acceptable salts or derivatives thereof.

5. The inert core of claim 3, wherein the pharmaceutically acceptable excipients comprise one or more of polymers, plasticizers, and binders.

6. An extended release dosage form of metoprolol or a salt thereof comprising the inert core of claim 1, wherein the inert core is further coated with a drug coating, said coating comprising metoprolol or a salt thereof, and wherein the drug coating is optionally further coated with one or more pharmaceutically acceptable rate-controlling polymers.

7. The extended release dosage form of claim 6, wherein the metoprolol is present in the form of metoprolol succinate.

8. The extended release dosage form of claim 6, wherein the rate-controlling polymer comprises one or more of cellulose ethers and acrylic acid polymers.

9. The extended release dosage form of claim 6, wherein the drug coating layer optionally comprises pharmaceutically acceptable excipients, said excipients comprising one or more of polymers, plasticizers, and binders.

10. The extended release dosage form of claim 6, wherein the extended release dosage form comprises a tablet, capsule, pellet, or sachet.

11. A dosage form comprising the inert core of claim 1, wherein the inert core is further coated with a drug coating, said coating comprising one or more pharmaceutically active ingredients and wherein the drug coating is optionally further coated with one or more pharmaceutically acceptable release controlling polymers and wherein said dosage form is coated with colloidal silicon dioxide.

12. The dosage form of claim 11, wherein the pharmaceutically active ingredient comprises metoprolol, and pharmaceutically acceptable salts or derivatives thereof.

13. The extended release dosage form of claim 11, wherein the drug coating layer optionally comprises pharmaceutically acceptable excipients, said excipients comprising one or more of polymers, plasticizers, and binders.

14. The dosage form of claim 11, wherein the pharmaceutically acceptable release controlling polymers comprises one or more of cellulose ethers and acrylic acid polymers.

15. The extended release dosage form of claim 6, wherein said dosage form is coated with colloidal silicon dioxide.

16. The extended release dosage form of claim 15, wherein the metoprolol is present in the form of metoprolol succinate.

17. The extended release dosage form of claim 15, wherein the dosage form comprises a tablet.

* * * * *